United States Patent [19]

Ward et al.

[11] 4,328,232
[45] * May 4, 1982

[54] BENZOQUINOLIZINES, ANTI-SECRETORY COMPOSITIONS CONTAINING THEM, AND METHODS OF TREATING ULCERS EMPLOYING THEM

[75] Inventors: Terence J. Ward, Slough; John F. White, Wokingham, both of England

[73] Assignee: John Wyeth & Brother Limited, Maidenhead, England

[*] Notice: The portion of the term of this patent subsequent to Nov. 25, 1997, has been disclaimed.

[21] Appl. No.: 201,661

[22] Filed: Oct. 27, 1980

[30] Foreign Application Priority Data

Nov. 7, 1979 [GB] United Kingdom ............. 38570/79

[51] Int. Cl.³ .................. A61K 31/47; C07D 455/06
[52] U.S. Cl. ................................. 424/258; 546/95
[58] Field of Search ........................ 546/95; 424/258

[56] References Cited

U.S. PATENT DOCUMENTS 4,235,910 11/1980 White et al. ................. 424/258

Primary Examiner—Donald G. Daus
Assistant Examiner—Diana G. Rivers
Attorney, Agent, or Firm—Richard K. Jackson

[57] ABSTRACT

The invention concerns benzoquinolizines of the general formula (I)

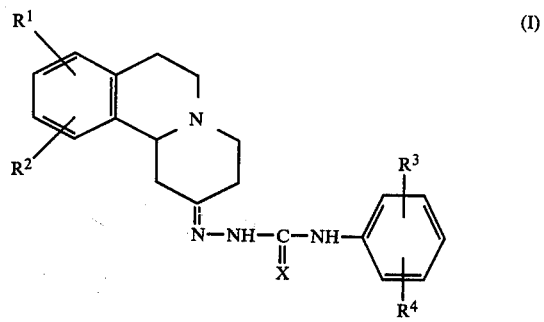

and the pharmaceutically acceptable acid addition salts thereof, wherein the

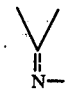

linkage represents a single bond linkage of formula

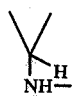

or a double bond linkage of formula

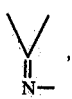

$R^1$ and $R^2$ which may be the same or different each represent hydrogen, lower alkyl, lower alkoxy or halogen, $R^3$ and $R^4$ which may be the same or different each represent hydrogen, halogen, lower alkyl, lower alkoxy, nitro, amino, lower alkylamino, di(lower)alkylamino or trifluoromethyl and X is O, S or NH. The compounds possess anti-secretory activity.

7 Claims, No Drawings

BENZOQUINOLIZINES, ANTI-SECRETORY COMPOSITIONS CONTAINING THEM, AND METHODS OF TREATING ULCERS EMPLOYING THEM

This invention relates to benzoquinolizines, to pharmaceutical compositions containing them, to the use of these benzoquinolizines and to processes for preparing them.

The present invention provides novel benzoquinolizines of the general formula (I)

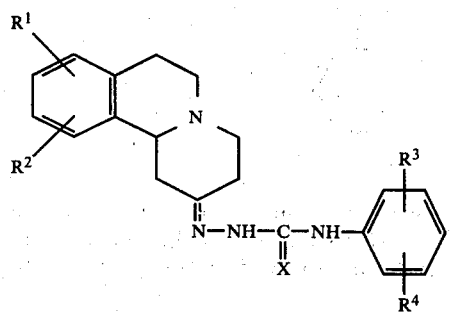

(I)

and the pharmaceutically acceptable acid addition salts thereof, wherein the

linkage represents a single bond linkage of formula

or a double bond linkage of formula

$R^1$ and $R^2$ which may be the same or different each represent hydrogen lower alkyl, lower alkoxy or halogen, $R^3$ and $R^4$ which may be the same or different each represent hydrogen, halogen, lower alkyl, lower alkoxy, nitro, amino, lower alkylamino, di(lower)alkylamino or trifluoromethyl and X is O, S or NH. Preferably X is NH.

When the

linkage represents the above defined single bond linkage the compounds of the invention are those of general formula (Ia)

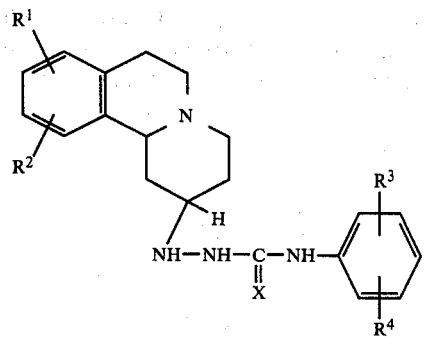

(Ia)

and their pharmaceutically acceptable acid addition salts.

When the

linkage represents the above defined double bond linkage the compounds of the invention are those of general formula (Ib)

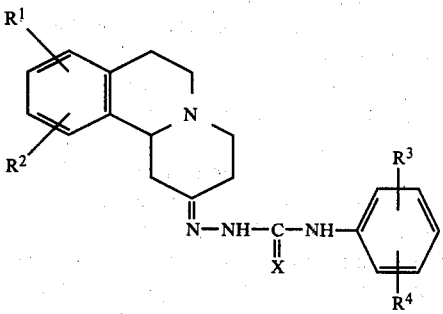

(Ib)

The term "lower" as used herein means that the radical referred to contains 1 to 6 carbon atoms. Preferably the radical contains 1 to 4 carbon atoms.

The groups $R^1$ and $R^2$ can be hydrogen, lower alkyl (e.g. methyl, ethyl, propyl, or butyl), lower alkoxy (e.g. methoxy, ethoxy, propoxy or butoxy) or halogen (e.g. fluorine, chlorine or bromine). Preferred meanings are those in which $R^1$ and $R^2$ are both hydrogen and those in which $R^1$ and $R^2$ are substituents in the 9 and 10-positions of the benzoquinolizine ring and are, for example, both lower alkoxy (e.g. methoxy).

The groups $R^3$ and $R^4$ can be hydrogen, halogen (e.g. fluorine, chlorine or bromine), lower alkyl (e.g. methyl, ethyl, propyl or butyl), lower alkoxy (e.g. methoxy, ethoxy, propoxy or butoxy), nitro, amino, lower alkylamino (e.g. methylamino), di(lower)alkylamino (e.g. dimethylamino) or trifluoromethyl. In preferred compounds $R^3$ and $R^4$ are in the 2 and 6-positions of the phenyl ring and are, for example, both halogen such as chlorine.

The componds of the invention in which X represents O are semicarbazones. When X represents S the compounds are thiosemicarbazones and when X represents NH the compounds are amidinohydrazones.

The compounds of the invention can be prepared by known processes for preparing semicarbazones, thiosemicarbazones or amidinohydrazones. For example the compounds of general formula (Ib) and their pharmaceutically acceptable acid addition salts may be prepared by reacting a ketone of general formula (II)

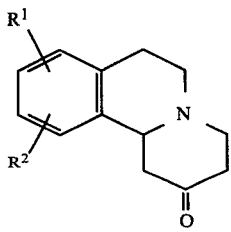
(II)

(wherein $R^1$ and $R^2$ have the meanings given above) with a compound of general formula (III)

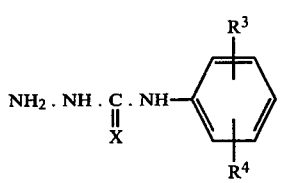
(III)

(wherein X, $R^3$ and $R^4$ have the meanings give above) or a salt thereof. If desired, the reaction can be carried out in presence of a catalyst e,g, a basic catalyst such as pyridine. The reaction is preferably carried out in an inert organic solvent. If necessary a reactive substituent group may be protected during the reaction and the protecting group removed at a later stage.

The compounds of general formula (Ia) and their pharmaceutically acceptable acid addition salts may be prepared by reduction of the compound of general formula (Ib) or their acid addition salts. The reduction can be carried out with reducing agents such as hydride transfer agents (e.g. lithium aluminium hydride), catalytic reduction (e.g. hydrogen with platininum or nickel catalyst) and a sodium/mercury couple.

In an alternative method of preparing the compounds of the invention a compound of general formula (IV)

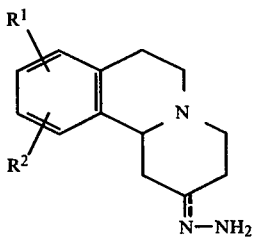
(IV)

(where $R^1$, $R^2$ and the linkage

are as defined above) may be reacted with an isocyanate or isothiocynate of formula

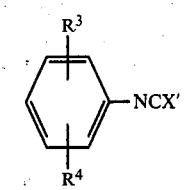
(Va)

(where $R^3$ and $R^4$ are as defined above and X' is oxygen or sulphur) or with an isothiourea derivative of formula (Vb)

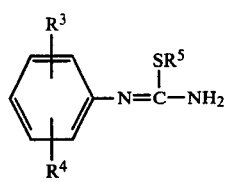
(Vb)

(where $R^3$ and $R^4$ have the meanings given above and $R^5$ is lower alkyl, preferably methyl). Preferably in the starting material of general formula (IV) the

linkage is

Once the compound of general formula (I) has been prepared by any of the above processes then, if necessary, a substituent in the molecule may be converted into another substituent specified in connection with general formula (I).

If in the processes described above the compound of the invention is obtained as an acid addition salt, the free base can be obtained by basifying a solution of the acid addition salt. Conversely, if the product of the process is a free base it may be converted into a pharmaceutically acceptable acid addition salt e.g. by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The starting materials for the above processes are known compounds or may be prepared by processes known for analogous compounds. For example the ketones of general formula (II) may be prepared by the procedures described, for example, in Beke et al, Chem. Ber., 1962, 95, 2132 and the compounds of general formula (IV) may be prepared from the ketones by, for example, the method described by G. R. Newkome and D. L. Fishel, J. Org. Chem., 1966, 31, 677.

The compounds of the invention possess one or more asymmetric carbon atoms and the compounds may be in the form of the pure enantiomorphs or mixtures of such enantiomorphs, such as racemates. Optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired compound (provided further chemical reaction does not cause racemisation).

The compounds of the present invention possess pharmacological activity. In particular they possess anti-secretory activity as indicated by standard pharmacological procedures e.g. the test of H. Shay, D. Sun and H. Greenstein, Gastroenterology, 1954 26, 903-13. For example, 1-[1,3,4,6,7,11bα-hexahydro-2H-benzo[a]quinolizin-2-ylidene]-4-(2,6-dichlorophenyl)amidinohydrazine and 1-[9,10-dimethoxy-1,3,4,6,7,11bα-hexahydro-2H-benzo[a]quinolizin-2-ylidene]-4-(2,6-dichlorophenyl)amidinohydrazine, representative compounds of the invention, show marked activity in this test procedure at dosages of 10 mg/kg intra-duodenally. Compounds possessing anti-secretory activity are used as anti-ulcer agents. Some of the compounds, in particular 1-[9,10-dimethoxy-1,3,4,5,6,7,11bα-hexahydro-2H-benzo[a]quinolizin-2-ylidene]-4-(2,6-dichlorophenyl)amidinohydrazine, also exhibit antihypertensive activity in standard pharmacological testing.

In one aspect the invention includes a pharmaceutical composition comprising a compound of general formula (I) or a pharmaceutically acceptable salt thereof in association with a pharmaceutically acceptable carrier. Any suitable carrier known in the art can be used to prepare the pharmaceutical composition. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The anti-ulcer compositions of the present invention may include one or more antacid ingredients, e.g. aluminium hydroxide, magnesium hydroxide, bismuth carbonate, aluminium glycinate, calcium carbonate, magnesium trisilicate, sodium bicarbonate or the alumina gel described in U.K. Patent Specification No. 1,284,394.

The following Examples illustrate the invention.

EXAMPLE I

1-[1,3,4,6,7,11bα-Hexahydro-2H-benzo[a]quinolizin-2-ylidene]-4-(2,6-dichlorophenyl)amidinohydrazine A mixture of 1,3,4,6,7,11bα-hexahydro-2H-benzo[a]quinolizin-2-one (0.637 g; 3.17 mM) and 2,6-dichlorophenylaminoquanidine hydroiodide (1.10 g; 3.17 mM; Chem. Abs. 83: P 163859q) in ethanol (10 cm$^3$) and pyridine (5 cm$^3$) was stirred and heated to reflux for 1.5 h. The solvents were evaporated in vacuo and the residue taken up into ethanol and acidified with ethanolic hydrogen chloride. After standing in the refrigerator overnight, the precipitated crystals were filtered, washed with ethanol, triturated with boiling methanol, cooled and re-filtered to give pure title compound as the dihydrochloride. Further precipitation from the mother liquors gave a large second crop which was purified in the same way. The crops were combined to give the product as colourless micro-needles (0.72 g), m.p. 230°–231° (dec).

Analysis: Found C, 50.37; H, 5.03; N, 14.92%. $C_{20}H_{21}Cl_2N_5.2HCl$ requires C, 50.54; H, 4.88; N, 14.74%.

EXAMPLE 2

1-[9,10-Dimethoxy-1,3,4,6,7,11bα-hexahydro-2H-benzo[a]quinolizin-2-ylidene]-4-(2,6-dichlorophenyl)amidinohydrazine A mixture of 1,3,4,6,7,11bα-hexahydro-9,10-dimethoxy-2H-benzo[a]quinolizin-2-one (1.31 g. 5 mM) and 2,6-dichlorophenylaminoguanidine hydroiodide (1.73 g 5 mM) in ethanol (20 cm³) and pyridine (10 cm³) was stirred and heated to reflux for 2 h. The solvents were evaporated from the clear solution on the rotary evaporator and the residue was dissolved in ethanol (20 cm³) and acidified strongly with ethanolic hydrogen chloride. After scratching well to induce crystallisation, then standing for 5 h, the precipitated crystals were collected by filtration and washed well with ethanol. The crystals were then triturated well with boiling ethanol (15 cm³) for 2 h, cooled, filtered and dried at 60° to give pure title compound as the dihydrochloride hemihydrate (1.58 g), pale cream crystals m.p. 231°–233° (dec), which yellowed slightly on standing in air.

Analysis: Found: C, 48.72; H, 5.27; N, 12.72%. $C_{22}H_{25}Cl_2N_5O_2.2HCl.\frac{1}{2}H_2O$ requires C, 48.54; H, 5.18; N, 12.87%.

EXAMPLE 3

1-(2,6-Dichlorophenyl)-4-(1,3,4,6,7,11bα-hexahydro-2H-benzo[a]quinolizin-2-yl)amidinohydrazine A stirred mixture of 1-[1,3,4,6,7,11bα-hexahydro-2H-benzo[a]quinolizin-2-ylidene]-4-(2,6-dichlorophenyl)amidinohydrazine (0.95 g; 2 mM) and lithium aluminum hydride (0.31 g; 8 mM) in dry tetrahydrofuran (50 cm³) was heated to reflux under dry nitrogen for 4 h. After cooling, the suspension was decomposed with water (3 cm³) and filtered. Evaporation of the filtrate gave a pale yellow glass (0.67 g.). This was dissolved in ethanol (10 cm³) and acidified with ethanolic hydrogen chloride. The solvent was evaporated and the residue recrystallised from isopropanol/ethyl acetate. A second crop was obtained by dilution of the liquors with ethyl acetate, and recrystallisation of the precipitate so obtained. Both crops were combined and dried at 70°/1 mm to give pure title compound as the dihydrochloride threequaterhydrate (0.21 g), yellow cyrstals, m.p. 237°–260° (dec).

Analysis: Found: C, 49.05; H, 5.51; N, 14.17%. $C_{20}H_{23}Cl_2N_5.2HCl.\frac{3}{4}H_2O$ requires C, 48.94; H, 5.44; N, 14.27%.

EXAMPLE 4

1-(1,3,4,6,7,11bα-Hexahydro-2H-benzo[a]quinolizin-2-ylidene)-4-phenylsemicarbazone and 1-(1,3,4,6,7,11bα-hexahydro-2-H-benzo[a]quinolizin-2-ylidene)-4-phenylthiosemicarbazone 1,3,4,6,7,11bα-Hexahydro-2H-benzo[a]quinolizine-2-one is reacted with 4-phenylsemicarbazide and 4-phenylthiosemicarbazide in ethanol-pyridine under reflux to give respectively the two title compounds.

We claim:

1. A compound selected from the group consisting of a benzoquinolizine of the formula (I)

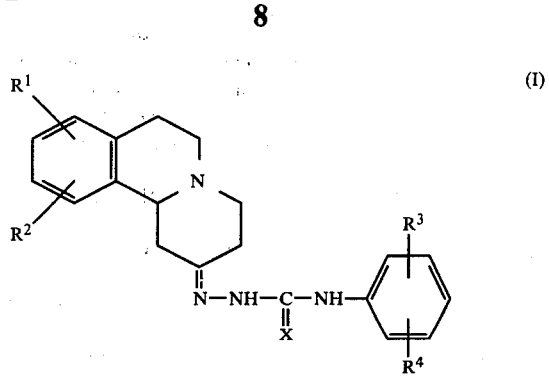

and a pharmaceutically acceptable acid addition salt thereof, wherein the

linkage represents a single bond linkage of the formula

or a double bond linkage of formula

$R^1$ and $R^2$ which may be the same or different each represent hydrogen, lower alkyl, lower alkoxy or halogen, $R^3$ and $R^4$ which may be the same or different each represent hydrogen, halogen, lower alkyl, lower alkoxy, nitro, amino, lower alkylamino, di(lower)alkylamino or trifluoromehyl and X is O, S or NH.

2. A compound according to claim 1 which is a benzoquinolizine of formula (Ib)

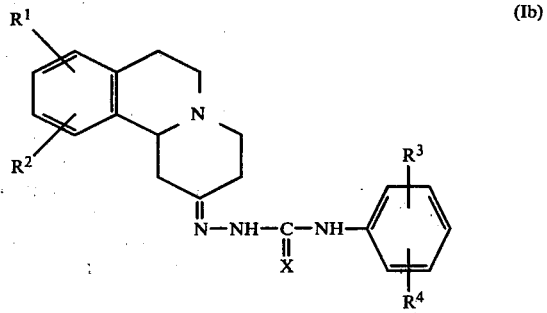

(where $R^1$, $R^2$, $R^3$ and $R^4$ are as defined in claim 1) or a pharmaceutically acceptable acid addition salt thereof.

3. A compound according to claim 1 which is 1-[1,3,4,6,7,11bα-hexahydro-2H-benzo[a]quinolizin-2-ylidene-9 -4-(2,6-dichlorophenyl)amidinohydrazine or a pharmaceutically acceptable acid addition salt thereof.

4. A compound according to claim 1 which is 1-[9,10-dimethoxy-1,3,4,6,7,11bα-hexahydro-2H-benzo[a]- quinolizin-2-ylidene]-4-(2,6-dichlorophenyl)amidinohydrazine or a pharmaceutically acceptable acid addition salt thereof.

5. A compound according to claim 1 which is 1-(2,6-dichlorophenyl)-4-(1,3,4,6,7,11bα-hexahydro-2H-benzo[a]quinolizin-2-yl)amidinohydrazine or a pharmaceutically acceptable acid addition salt thereof.

6. A pharmaceutical composition having anti-secretory activity which comprises a compound selected from the group consisting of a benzoquinolizine of the formula (I)

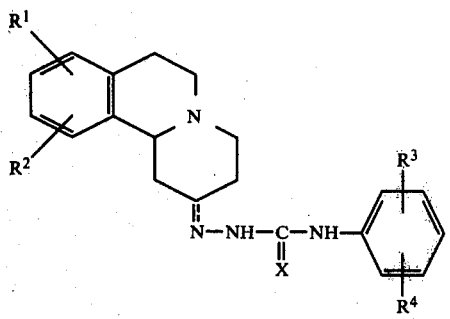

and a pharmaceutically acceptable acid addition salt thereof, where in the

linkage represents a single bond linkage of formula

or a double bond linkage of formula

$R^1$ and $R^2$ which may be the same or different each represent hydrogen, lower alkyl, lower alkoxy or halogen, $R^3$ and $R^4$ which may be the same or different each represent hydrogen, halogen, lower alkyl, lower alkoxy, nitro, amino, lower alkylamino, di(lower)alkylamino or trifluoromethyl and X is O, S or NH.

7. A method of treating ulcers in warm blooded mammal which comprises administering to said mammal an antisecretory effective amount of a compound selected from the group consisting of a benzoquinolizine of the formula (I)

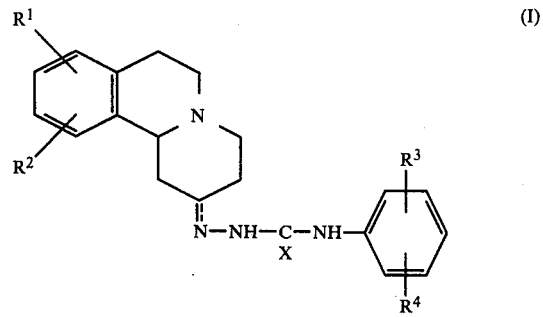

and a pharmaceutically acdeptable acid addition salt thereof, wherein the

linkage represents a single bond linkage of the formula

or a double bond linkage of formula

$R^1$ and $R^2$ which may be the same or different each represent hydrogen, lower alkyl, lower alkoxy or halogen, $R^3$ and $R^4$ which may be the same or different each represent hydrogen, halogen, lower alkyl, lower alkoxy, nitro, amino, lower alkylamino, di(lower)alkylamino or trifluoromethyl and X is O, S or NH.

* * * * *